(12) United States Patent
Akassoglou

(10) Patent No.: US 8,877,195 B2
(45) Date of Patent: Nov. 4, 2014

(54) MONOCLONAL ANTIBODIES TO FIBRIN

(75) Inventor: Katerina Akassoglou, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/425,020

(22) Filed: Mar. 20, 2012

(65) Prior Publication Data

US 2012/0183560 A1 Jul. 19, 2012

Related U.S. Application Data

(63) Continuation of application No. PCT/US2010/050873, filed on Sep. 30, 2010.

(60) Provisional application No. 61/248,014, filed on Oct. 2, 2009.

(51) Int. Cl.
*A61K 39/395* (2006.01)

(52) U.S. Cl.
USPC ............... 424/145.1; 424/133.1; 530/388.25; 530/387.3; 530/382; 530/300

(58) Field of Classification Search
None
See application file for complete search history.

(56) References Cited

U.S. PATENT DOCUMENTS

| | | |
|---|---|---|
| 2003/0031675 A1 | 2/2003 | Mikesell et al. |
| 2008/0226652 A1 | 9/2008 | Bakker et al. |
| 2009/0221507 A1 | 9/2009 | Akassoglou |
| 2012/0093812 A1* | 4/2012 | Akassoglou ............... 424/133.1 |

FOREIGN PATENT DOCUMENTS

WO　　WO 2007/038407　　*　4/2007

OTHER PUBLICATIONS

Paul, Fundamental Immunology, 3rd Edition, 1993, pp. 292-295, under the heading "Fv Structure and Diversity in Three Dimensions".*
Pascalis et al. Grafting of "abbreviated" complementarity-determining regions containing specificity-determining residues essential for ligand contact to engineer a less immunogenic humanized monoclonal antibody. J. Immunol. 2002, 169:3076-3084.*
Ryu et al., 2009, "Fibrinogen Signal Transduction in the Nervous System," Journal of Thrombosis and Haemostasis, 7 (Suppl. 1):151-154.
Ryu et al., 2009, "A Leaky Blood-Brain Barrier, Fibrinogen Infiltration and Microglial Reactivity in Inflamed Alzheimer's Disease Brain," J. Cell. Mol. Med., 13(9A):2911-2925.
European Supplementary Search Report for EP Application No. 10821238.2 mailed May 28, 2013 (7 pages).
Hu et al., 2001, "Molecular Basis of Biomaterial-Mediated Foreign Body Reactions," Blood, 98(4):1231-1238.
Patent Search Report issued by the Eurasian Patent Office on Aug. 24, 2012.
Altieri et al., 1993, "The Structural Motif Glycine 190-Valine 202 of the Fibrinogen y Chain Interacts with CD11b/CD18 Integrin (αMβ2, Mac-1) and Promotes Leukocyte Adhesion," The Journal of Biological Chemistry, 268 (3):1847-1853.
Adams et al., 2007, "The fibrin-derived y377-395 peptides inhibits microglia activation and suppresses relapsing paralysis in central nervous system autoimmunie disease," The Journal of Experimental Medicine, 204(3):571-582.
PCT Search Report and Written Opinion for PCT/US2010/050873 mailed Dec. 15, 2010.
Chilean Search Report for Chilean Application No. 788-2012 mailed Jul. 25, 2013 (17 pages).
Brown, et al., 1996, "Tolerance to Single, but not Multiple, Amino Acid Replacements in Antibody VH CDR2," The Journal of Immunology, 3285-3291.
Davies et al., 1996, "Affinity Improvement of Single Antibody VH Domains: Residues in all Three Hypervariable Regions Affect Antigen Binding," Immunotechnology 2:169-179.
Giusti et al., 1987, "Somatic Diversification of S107 from an Antiphosphocholine to an Anti-DNA Autoantibody is Due to a Single Base Change in its Heavy Chain Variable Region," Proc. Natl. Acad. Sci. USA, 84:2926-2930.
Holt et al., 2003, "Domain Antibodies: Proteins for Therapy," Trends in Biotechnology, 21(11):484-490.
Kussie et al., 1994, "A Single Engineered Amino Acid Substitution Changes Antibody Fine Specificity," Journal of Immunology, 146-152.
Liu et al., 1999, "Fine Mapping of the Antigen-Antibody Interaction of scFv215, a Recombinant Antibody Inhibiting RNA Polymerase II from *Drosophila melanogaster*," Journal of Molecular Recognition, 12:103-111.
Maynard et al., 2000, "Antibody Engineering," Annu. Rev. Biomed. Eng. 02:339-76.
Pini et al., 1998, "Design and Use of a Phage Display Library," The Journal of Biological Chemistry, 273 (34):21769-21776.
Rudikoff et al., 1982, "Single Amino Acid Substitution Altering Antigen-Binding Specificity," Proc. Natl. Acad. Sci. USA, 79:1979-1983.
Schildbach et al., 1994, "Contribution of a Single Heavy Chain Residue to Specificity of an Anti-Digoxin Monoclonal Antibody," Protein Science, 3:737-749.
Schildbach et al., 1993, "Heavy Chain Position 50 is a Determinant of Affinity and Specificity for the Anti-digoxin Antibody 26-10," The Journal of Biological Chemistry, 268(29):21739-21747.
Vajdos et al., 2002, "Comprehensive Functional Maps of the Antigen-binding Site of an Anti-ErbB2 Antibody Obtained with Shotgun Scanning Mutagenesis," J. Mol. Biol., 320:415-428.
Xiang et al., 2000, "Study of B72.3 Combining Sites by Molecular Modeling and Site-Directed Mutagenesis," Protein Engineering, 13(5):339-344.
Lishko et al., 2004, "Multiple Binding Sites in Fibrinogen for Integrin αMβ2 (Mac-1)," The Journal of Biological Chemistry, 279(43):44897-44906.
Chilean Office Action for Chilean Application No. 788-2012.

* cited by examiner

*Primary Examiner* — Dong Jiang
(74) *Attorney, Agent, or Firm* — Sutherland Asbill & Brennan LLP

(57) ABSTRACT

The present invention provides an isolated antibody that binds a fibrin or fibrinogen γC domain. In various aspects, the antibody inhibits microglial adhesion to the fibrin or fibrinogen γC domain, inhibits Mac-1 binding to the fibrin or fibrinogen γC domain, and/or suppresses clinical symptoms of Experimental Autoimmune Encephalomyelitis (EAE). Various methods of using the antibodies, pharmaceutical compositions, kits, vectors, cells comprising the vectors, and antibody generating methods are provided.

22 Claims, 5 Drawing Sheets

```
                       SEQUENCE LISTING

<160> NUMBER OF SEQ ID NOS: 18

<210> SEQ ID NO 1
<211> LENGTH: 158
<212> TYPE: PRT
<213> ORGANISM: Mus musculus

<400> SEQUENCE: 1

Thr Phe Asp Ser Pro Tyr Gln Val Arg Arg Met Arg Phe Ser Ala Gln
1               5                  10                  15

Leu Leu Gly Leu Leu Val Leu Trp Ile Pro Gly Ser Thr Ala Asp Ile
            20                  25                  30

Val Met Thr Gln Ala Ala Phe Ser Asn Pro Ile Thr Leu Gly Thr Ser
        35                  40                  45

Ala Ser Met Ser Cys Arg Ser Ser Lys Ser Leu Leu His Ser Ser Gly
    50                  55                  60

Ile Thr Tyr Leu Ser Trp Tyr Leu Gln Lys Pro Gly Gln Ser Pro Gln
65                  70                  75                  80

Leu Leu Ile Tyr Gln Met Ser Asn Leu Ala Ser Gly Val Pro Asp Arg
                85                  90                  95

Phe Ser Ser Ser Gly Ser Gly Thr Asp Phe Thr Leu Arg Ile Ser Arg
            100                 105                 110
```

```
Val Glu Ala Glu Asp Val Gly Val Tyr Tyr Cys Ala Gln Asn Leu Glu
            115                 120                 125

Leu Pro Leu Thr Phe Gly Ala Gly Thr Lys Leu Glu Leu Lys Arg Ala
    130                 135                 140

Asp Ala Ala Pro Thr Val Ser Ala Cys Thr Lys Gly Glu Phe
145                 150                 155

<210> SEQ ID NO 2
<211> LENGTH: 16
<212> TYPE: PRT
<213> ORGANISM: Mus musculus

<400> SEQUENCE: 2

Arg Ser Ser Lys Ser Leu Leu His Ser Ser Gly Ile Thr Tyr Leu Ser
1               5                   10                  15

<210> SEQ ID NO 3
<211> LENGTH: 7
<212> TYPE: PRT
<213> ORGANISM: Mus musculus

<400> SEQUENCE: 3

Gln Met Ser Asn Leu Ala Ser
1               5

<210> SEQ ID NO 4
<211> LENGTH: 9
<212> TYPE: PRT
<213> ORGANISM: Mus musculus

<400> SEQUENCE: 4

Ala Gln Asn Leu Glu Leu Pro Leu Thr
1               5

<210> SEQ ID NO 5
<211> LENGTH: 166
<212> TYPE: PRT
<213> ORGANISM: Mus musculus

<400> SEQUENCE: 5

Asn Thr Ala Phe Ala Gly Phe Gly Arg Asn Met Arg Ser Leu Phe Ser
1               5                   10                  15

Leu Gln Leu Leu Ser Thr Gln Asp Leu Ala Met Gly Trp Ser Cys Ile
            20                  25                  30

Ile Val Leu Leu Val Ser Thr Ala Thr Gly Val His Ser Gln Val Gln
            35                  40                  45

Leu Gln Gln Pro Gly Ala Glu Leu Val Arg Pro Gly Thr Ser Val Lys
    50                  55                  60

Leu Ser Cys Lys Ala Ser Gly Tyr Thr Phe Thr Ser Tyr Trp Ile His
65                  70                  75                  80

Trp Val Lys Gln Arg Pro Gly Gln Gly Leu Glu Trp Ile Gly Leu Ile
                85                  90                  95

Asp Pro Ser Asp Ser Tyr Thr Asn Tyr Asn Gln Lys Phe Arg Gly Lys
            100                 105                 110

Ala Thr Leu Thr Val Asp Thr Ser Ser Thr Ala Tyr Met Gln Leu
            115                 120                 125

Ser Ser Leu Thr Ser Glu Asp Ser Ala Val Tyr Tyr Cys Ala Ser Ser
    130                 135                 140

Asp Pro Thr Gly Cys Trp Gly Gln Gly Thr Thr Leu Thr Val Ser Pro
145                 150                 155                 160
```

```
Ala Ser Thr Thr Pro Pro
            165

<210> SEQ ID NO 6
<211> LENGTH: 10
<212> TYPE: PRT
<213> ORGANISM: Mus musculus

<400> SEQUENCE: 6

Gly Tyr Thr Phe Thr Ser Tyr Trp Ile His
1               5                   10

<210> SEQ ID NO 7
<211> LENGTH: 17
<212> TYPE: PRT
<213> ORGANISM: Mus musculus

<400> SEQUENCE: 7

Leu Ile Asp Pro Ser Asp Ser Tyr Thr Asn Tyr Asn Gln Lys Phe Arg
1               5                   10                  15
Gly

<210> SEQ ID NO 8
<211> LENGTH: 6
<212> TYPE: PRT
<213> ORGANISM: Mus musculus

<400> SEQUENCE: 8

Ser Asp Pro Thr Gly Cys
1               5

<210> SEQ ID NO 9
<211> LENGTH: 474
<212> TYPE: DNA
<213> ORGANISM: Mus musculus

<400> SEQUENCE: 9
acttttgact caccatatca agttcgcaga atgaggttct ctgctcagct tctggggctg    60
cttgtgctct ggatccctgg atccactgca gatattgtga tgacgcaggc tgcattctcc   120
aatccaatca ctcttggaac atcagcttcc atgtcctgca ggtctagtaa gagtctccta   180
catagtagtg gcatcactta tttgtcttgg tatctgcaga agccaggcca gtctcctcag   240
ctcctgattt atcagatgtc aaccttgcc tcaggagtcc cagacaggtt cagtagcagt    300
gggtcaggaa ctgatttcac actgagaatt agccgagtgg aggctgagga tgtgggtgtt   360
tattactgtg ctcaaaatct agaacttccg ctcacgttcg gtgctgggac caagctggag   420
ctgaaacggg ctgatgctgc accaactgta tccgcatgca ccaagggcga attc          474

<210> SEQ ID NO 10
<211> LENGTH: 499
<212> TYPE: DNA
<213> ORGANISM: Mus musculus

<400> SEQUENCE: 10
gaacactgcg tttgctggct ttggaagaaa catgagatca ctgttctctc tacagttact    60
gagcacacag gacctcgcca tgggatggag ctgtatcatt gtcctcttgg tatcaacagc   120
tacaggtgtc cactcccagg tccaactgca gcagcctggg gctgagctgg tgaggcctgg   180
gacttcagtg aagttgtcct gcaaggcttc tggctacacc ttcaccagct actggataca   240
```

```
ctgggtaaag cagaggcctg acaaggcct tgagtggatc ggactgattg atccttctga      300
tagttatact aactacaatc aaaagttcag gggcaaggcc acattgactg tagacacatc      360
ctccagcaca gcctacatgc agctcagcag cctgacatct gaggactctg cggtctatta      420
ctgtgcaagc tccgatccta caggctgctg gggccaaggc accactctca cagtctcccc      480
agctagcaca acaccccca                                                   499
```

```
<210> SEQ ID NO 11
<211> LENGTH: 48
<212> TYPE: DNA
<213> ORGANISM: Mus musculus

<400> SEQUENCE: 11
aggtctagta agagtctcct acatagtagt ggcatcactt atttgtct                   48

<210> SEQ ID NO 12
<211> LENGTH: 21
<212> TYPE: DNA
<213> ORGANISM: Mus musculus

<400> SEQUENCE: 12
cagatgtcca accttgcctc a                                                21

<210> SEQ ID NO 13
<211> LENGTH: 27
<212> TYPE: DNA
<213> ORGANISM: Mus musculus

<400> SEQUENCE: 13
gctcaaaatc tagaacttcc gctcacg                                          27

<210> SEQ ID NO 14
<211> LENGTH: 30
<212> TYPE: DNA
<213> ORGANISM: Mus musculus

<400> SEQUENCE: 14
ggctacacct tcaccagcta ctggatacac                                       30

<210> SEQ ID NO 15
<211> LENGTH: 51
<212> TYPE: DNA
<213> ORGANISM: Mus musculus

<400> SEQUENCE: 15
ctgattgatc cttctgatag ttatactaac tacaatcaaa agttcagggg c               51

<210> SEQ ID NO 16
<211> LENGTH: 18
<212> TYPE: DNA
<213> ORGANISM: Mus musculus

<400> SEQUENCE: 16
tccgatccta caggctgc                                                    18

<210> SEQ ID NO 17
<211> LENGTH: 14
<212> TYPE: PRT
<213> ORGANISM: Mus musculus

<400> SEQUENCE: 17

Cys Gly Trp Thr Val Leu Gln Lys Arg Ile Asp Gly Ser Leu
```

```
                 1               5                    10

<210> SEQ ID NO 18
<211> LENGTH: 17
<212> TYPE: PRT
<213> ORGANISM: Mus musculus

<400> SEQUENCE: 18

Cys Lys Lys Thr Thr Met Lys Ile Ile Pro Phe Asn Arg Leu Thr Ile
1               5                   10                  15

Gly
```

MONOCLONAL ANTIBODIES TO FIBRIN

CROSS REFERENCES TO RELATED APPLICATIONS

Figure 1:
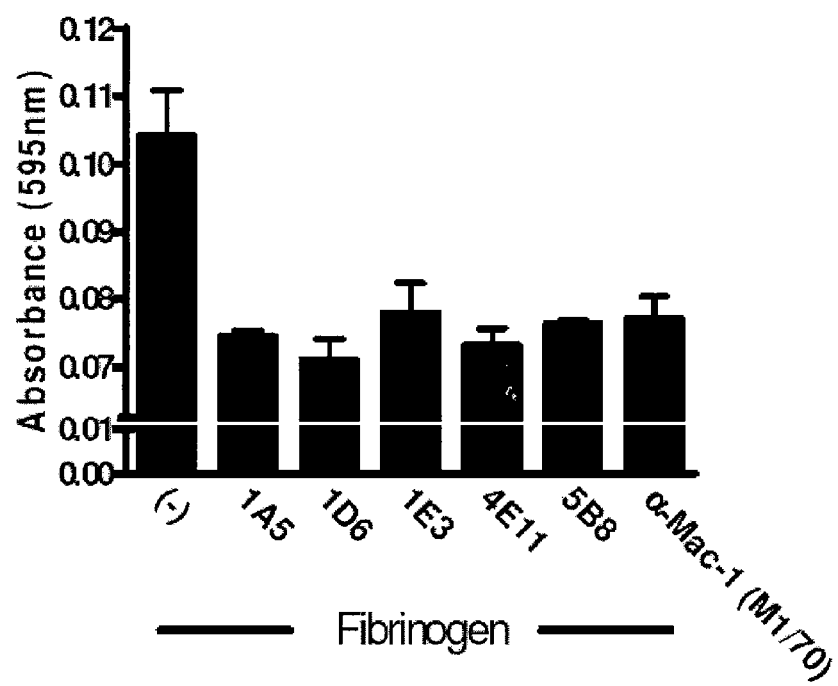

This patent application is a continuation of PCT Application No. PCT/US2010/050873, filed Sep. 30, 2010, which claims priority benefit of U.S. Provisional Application No. 61/248,014 filed Oct. 2, 2009, each of which is incorporated herein by reference in their entireties.

STATEMENT REGARDING FEDERALLY SPONSORED RESEARCH OR DEVELOPMENT

This invention was made in part with government support under NS052189 awarded by National Institute of Health. The government has certain rights in the invention.

INCORPORATION-BY-REFERENCE OF MATERIAL SUBMITTED ELECTRONICALLY

The Sequence Listing, which is a part of the present disclosure, includes the sequences provided in a document titled "RUC110WO_ST25" generated by U.S. Patent & Trademark Office Patent In Version 3.5 software comprising nucleotide and/or amino acid sequences of the present invention. The subject matter of the Sequence Listing is incorporated herein by reference in its entirety.

FIELD

This invention relates generally to the generation of monoclonal antibodies, and in particular, to monoclonal antibodies that recognize the fibrin γC domain, and to methods of using the monoclonal antibodies as therapeutics.

INTRODUCTION

Multiple sclerosis occurs when the immune system attacks the brain and spinal cord, damaging the myelin that insulates and protects nerve fibers. Brain cells known as microglia participate in this attack and are activated when the blood brain barrier (BBB) the lining of cells that should protect the brain from intruders breaks down. As the BBB breaks down, a blood protein called fibrinogen leaks into the brain. In addition to its known role in blood clotting, fibrinogen activates microglia cells and thus augments the inflammatory response in animal models of Multiple Sclerosis. In addition, it has been determined that fibrinogen is involved in the pathogenesis of certain cancers, rheumatoid arthritis and other diseases and pathologies in which tissue damage occurs whereby fibrinogen "leaks". See, e.g., Akassoglou et al., 2002, Neuron, 33:861-875; Akassoglou et al., 2004, Proc. Natl. Acad. Sci. USA, 101:6698-6703; Adams et al., 2007, J. Exp. Med., 35:2428-34. It has also been determined that the specific receptor, Mac-1, that fibrinogen utilizes to mediate these effects is not involved in the beneficial clotting properties of fibrinogen. However, to date, no specific inhibitors of fibrinogen/Mac-1 binding have been developed.

Therefore, what is needed are specific inhibitors of fibrinogen/Mac-1 binding that reduce the pro-inflammatory affects of fibrinogen in the brain and elsewhere in a subject while at the same time retaining the beneficial affects of fibrinogen in blood clotting.

SUMMARY

The present invention provides an isolated antibody that binds a fibrin or fibrinogen γC domain. In certain aspects of the invention, the antibody exhibits greater than 20% inhibition of microglial adhesion to the fibrin or fibrinogen γC domain. In another aspect, the antibody exhibits greater than 50% inhibition of Mac-1 binding to the fibrin or fibrinogen γC domain. In yet another aspect, the antibody suppresses clinical symptoms of Experimental Autoimmune Encephalomyelitis (EAE) at the time of the relapse.

In various embodiments, the antibody binds an $\gamma^{377-395}$ epitope of the fibrin or fibrinogen γC domain. The antibody of the invention can alternatively bind an $\gamma^{190-202}$ epitope of the fibrin or fibrinogen γC domain. Such antibodies are monoclonal antibodies, and in various aspects humanized antibodies or human antibodies.

In various aspects of the invention, the antibody comprises a light chain with three complementarity determining regions comprising an amino acid sequence including RSSKSLLHSSGITYLS (SEQ ID NO:2), QMSNLAS (SEQ ID NO:3), and AQNLELPLT (SEQ ID NO:4). In various aspects, the antibody comprises a heavy chain with three complementarity determining regions comprising an amino acid sequence including GYTFTSYWIH (SEQ ID NO:6), LIDPSDSYTNYNQKFRG (SEQ ID NO:7), and SDPTGC (SEQ ID NO:8). In certain instances, the antibody comprises a light chain with three complementarity determining regions comprising an amino acid sequence including RSSKSLLHSSGITYLS (SEQ ID NO:2), QMSNLAS (SEQ ID NO:3), and AQNLELPLT (SEQ ID NO:4) and a heavy chain with three complementarity determining regions comprising an amino acid sequence including GYTFTSYWIH (SEQ ID NO:6), LIDPSDSYTNYNQKFRG (SEQ ID NO:7), and SDPTGC (SEQ ID NO:8).

In various aspects, the antibodies above comprise a light chain variable amino acid sequence of SEQ ID NO:1. In various aspects, the antibodies above comprise a heavy chain variable amino acid sequence of SEQ ID NO:5. In yet another aspect, the antibodies above, comprise both a light chain variable amino acid sequence of SEQ ID NO:1 and a heavy chain variable amino acid sequence of SEQ ID NO:5.

In yet another aspect of the present invention, the antibodies above comprise, individually, a light chain with three complementarity determining regions comprising an amino acid sequence having at least 80% sequence identity to the sequences including RSSKSLLHSSGITYLS (SEQ ID NO:2), QMSNLAS (SEQ ID NO:3), and AQNLELPLT (SEQ ID NO:4) and a heavy chain with three complementarity determining regions comprising an amino acid sequence having at least 80% sequence identity to the sequences including GYTFTSYWIH (SEQ ID NO:6), LIDPSDSYTNYNQKFRG (SEQ ID NO:7), and SDPTGC (SEQ ID NO:8); and wherein the light chain complementarity domains and heavy chain complementarity domains retain Mac-1 binding ability.

In yet another aspect of the present invention, the antibodies above comprise, individually, a light chain with three complementarity determining regions comprising an amino acid sequence having at least 90% sequence identity to the sequences including RSSKSLLHSSGITYLS (SEQ ID NO:2), QMSNLAS (SEQ ID NO:3), and AQNLELPLT (SEQ ID NO:4) and a heavy chain with three complementarity determining regions comprising an amino acid sequence having at least 90% sequence identity to the sequences including GYTFTSYWIH (SEQ ID NO:6), LIDPSDSYTNYNQKFRG (SEQ ID NO:7), and SDPTGC (SEQ ID NO:8); and wherein the light chain complementarity domains and heavy chain complementarity domains retain Mac-1 binding ability.

In yet another aspect of the present invention, the antibodies above comprise, individually, a light chain with three complementarity determining regions comprising an amino acid sequence having at least 95% sequence identity to the sequences including RSSKSLLHSSGITYLS (SEQ ID NO:2), QMSNLAS (SEQ ID NO:3), and AQNLELPLT (SEQ ID NO:4) and a heavy chain with three complementarity determining regions comprising an amino acid sequence having at least 95% sequence identity to the sequences including GYTFTSYWIH (SEQ ID NO:6), LIDPSDSYTNYNQK-FRG (SEQ ID NO:7), and SDPTGC (SEQ ID NO:8); and wherein the light chain complementarity domains and heavy chain complementarity domains retain Mac-1 binding ability.

In yet another aspect of the present invention, the antibodies above comprise, individually, a light chain with three complementarity determining regions comprising an amino acid sequence having at least 99% sequence identity to the sequences including RSSKSLLHSSGITYLS (SEQ ID NO:2), QMSNLAS (SEQ ID NO:3), and AQNLELPLT (SEQ ID NO:4) and a heavy chain with three complementarity determining regions comprising an amino acid sequence having at least 99% sequence identity to the sequences including GYTFTSYWIH (SEQ ID NO:6), LIDPSDSYTNYNQK-FRG (SEQ ID NO:7), and SDPTGC (SEQ ID NO:8); and wherein the light chain complementarity domains and heavy chain complementarity domains retain Mac-1 binding ability.

A method is also provided for alleviating a symptom of a pathology associated with Mac-1 binding to fibrin or Mac-1 binding with fibrinogen, the method comprising administering the antibody of claim 1 to a subject in which such alleviation is desired in an amount sufficient to alleviate the symptom of the pathology in the subject. In various aspects of this method, the subject is a human. In various aspects, the pathology includes multiple sclerosis, spinal cord injury, Alzheimer's Disease, stroke, Rheumatoid Arthritis and cancer:

A pharmaceutical composition is also provided comprising the antibodies above and a pharmaceutically acceptable carrier. In another aspect, a kit is provided comprising the antibodies above. In yet another aspect, a vector is provided comprising a nucleic acid sequence encoding a fibrin $\gamma^{377-395}$ epitope, CKKTTMKIIPFNRLTIG (SEQ ID NO:18), or a biologically active derivative thereof. In another aspect, a cell is provided comprising the vector.

In yet another aspect of the invention, a method is provided for generating an antibody that immunospecifically binds to a fibrin $\gamma^{377-395}$ epitope, or a biologically active derivative thereof, the method comprising: administering to a subject a first dosage of the cell, wherein the first dosage is sufficient to generate an immune response in said subject. In various aspects, the method can further comprise the step of administering to said subject a second dosage of said cell, wherein said second dosage is sufficient to generate an immune response in said subject. In various aspects, the antibody produced inhibits fibrin/Mac-1 binding in said subject.

In another aspect, a method is provided for screening for a ligand that binds a Mac-1 receptor and modulates Mac-1 receptor activity, the method comprising: (a) providing the antibody of claim 1; (b) contacting a fibrin $\gamma^{377-395}$ epitope CKKTTMKIIPFNRLTIG (SEQ ID NO:18), or a biologically active derivative thereof, and forming an antibody/polypeptide complex; (c) contacting the antibody/polypeptide complex with a composition comprising a candidate compound; and (d) determining whether the candidate compound binds the monoclonal antibody; whereby, binding of the candidate compound indicates that said candidate compound is a ligand that modulates Mac-1 receptor activity.

These and other features, aspects and advantages of the present teachings will become better understood with reference to the following description, examples and appended claims.

DRAWINGS

Those of skill iii the art will understand that the drawings, described below, are for illustrative purposes only. The drawings are not intended to limit the scope of the present teachings in any way.

FIG. 1. Monoclonal antibody binding as assessed by absorbance measurements at 595 nm compared to commercially available blocking antibody to Mac-1 (M1/70).

Figure 2:
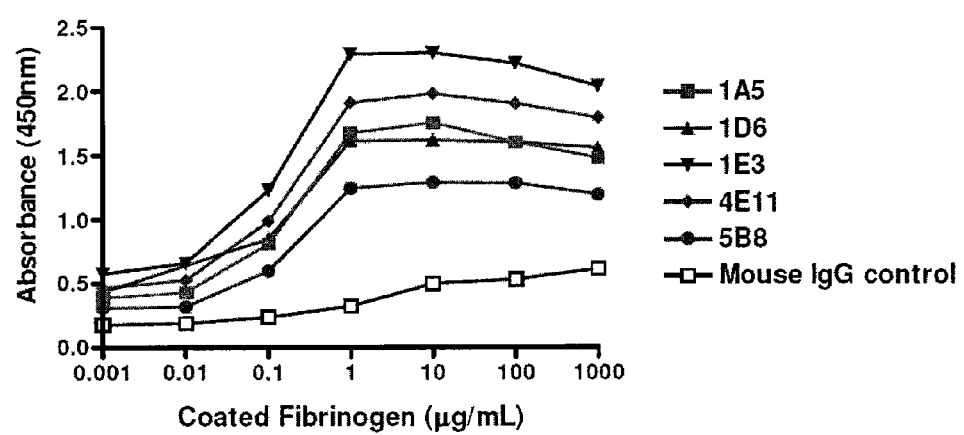

FIG. 2. Results of ELISA measuring monoclonal antibody binding to fibrinogen.

Figure 3:
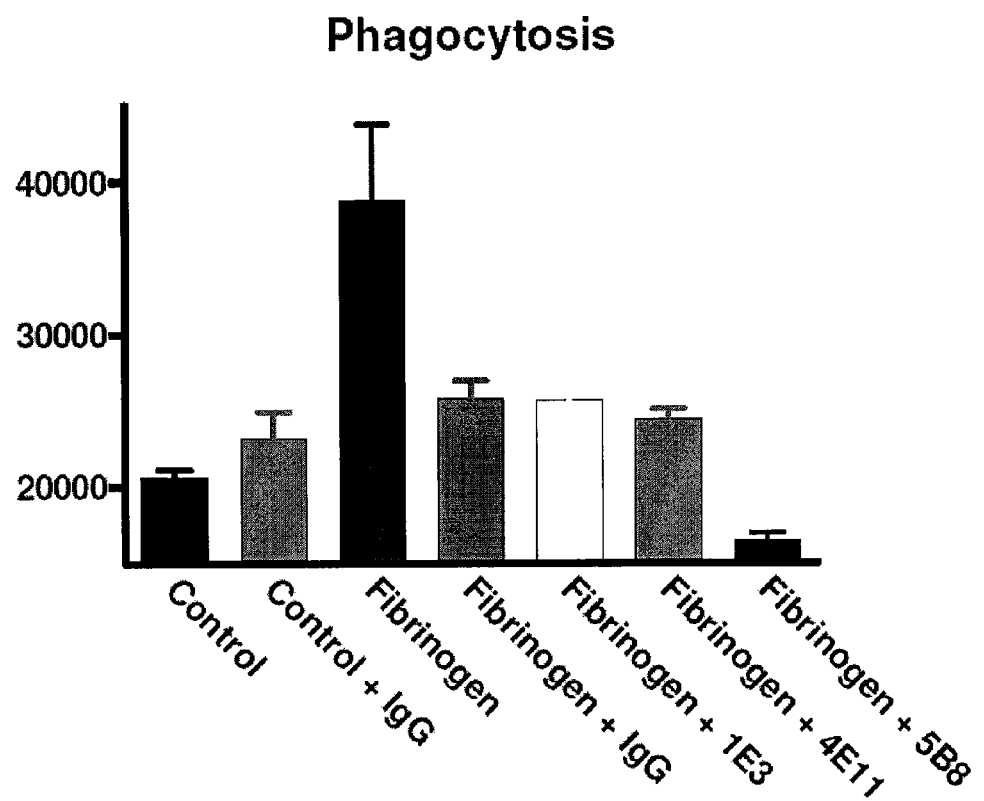

FIG. 3. The monoclonal antibody 5B8 against the modified fibrin $\gamma^{377-395}$ epitope shows increased efficacy in inhibiting phagocytosis.

Figure 4A:
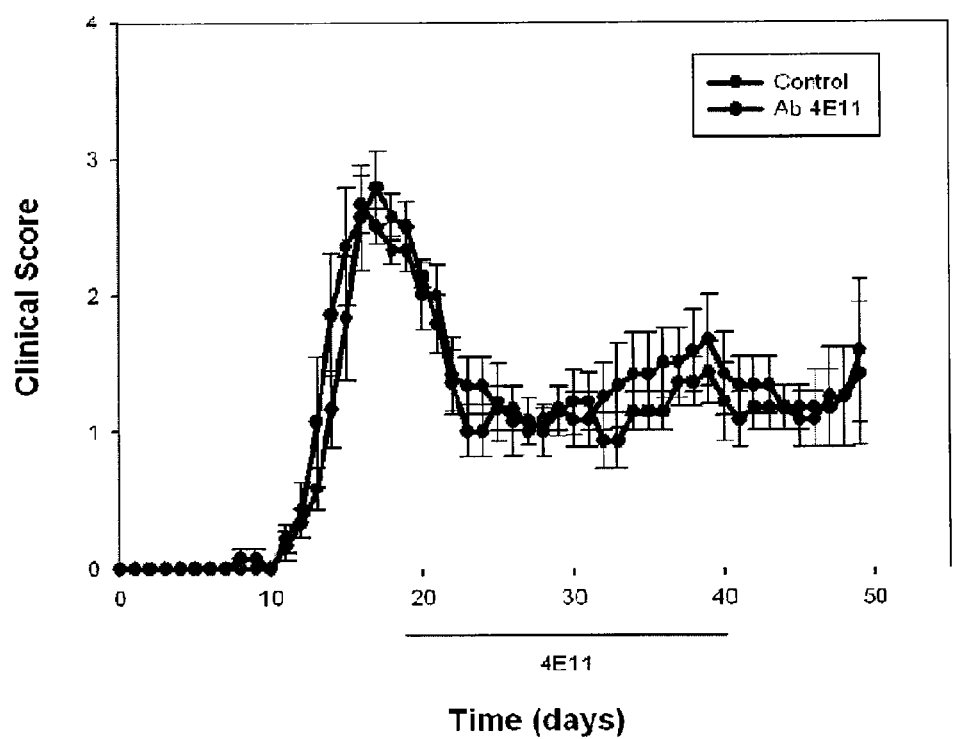
Figure 4B:
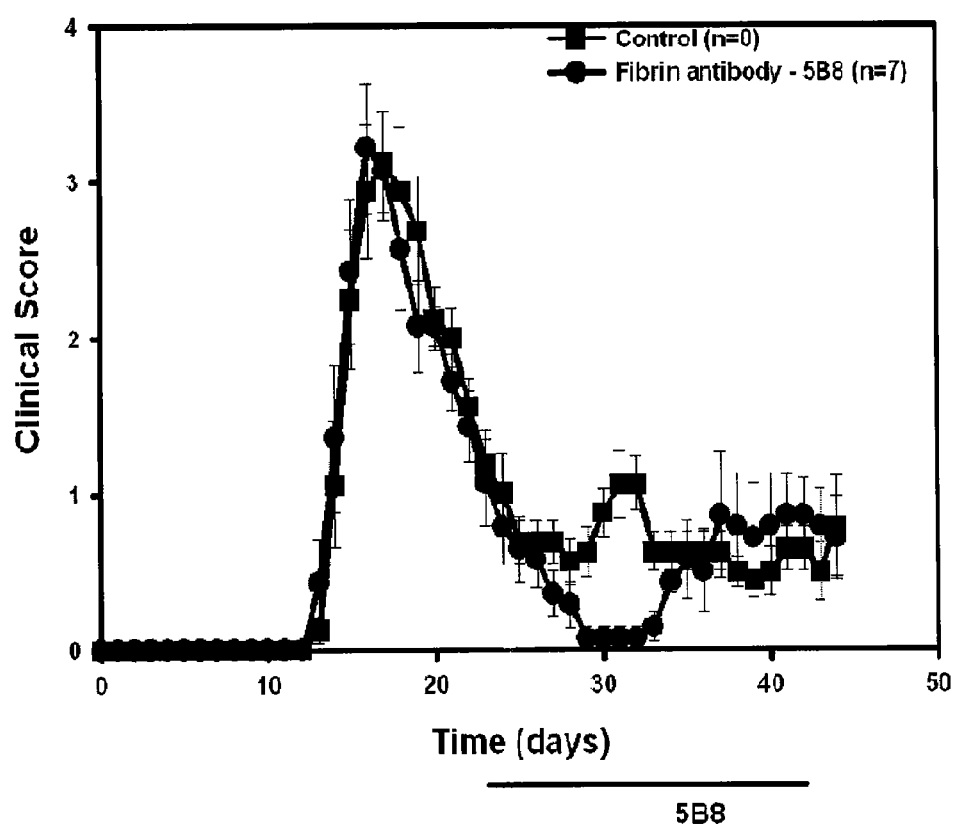

FIG. 4. In vivo experiments of administration of anti-fibrin antibodies in PLP EAE after the first incidence of clinical symptoms related to antibodies (A) 4E11 and (B) 5B8. The monoclonal antibody 5B8 shows suppression at the time of relapse.

DETAILED DESCRIPTION

Abbreviations and Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligonucleotide or polynucleotide chemistry and hybridization described herein are those well known and commonly used in the art. Standard techniques are used for recombinant DNA, oligonucleotide synthesis, tissue culture and cell transformation. Enzymatic reactions and purification techniques are performed using commercially available kits according to manufacturer's specifications or as commonly accomplished in the art or as described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as Molecular Cloning: A Laboratory Manual, second edition (Sambrook et al., 1989) Cold Spring Harbor Press; Oligonucleotide Synthesis (M J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C A. Janeway and P. Travers, 1997); Antibodies (P. Finch, 1997); Antibodies: apractical approach (D. Catty., ed., IRL Press, 1988-1989); Monoclonal antibodies: apractical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

The nomenclatures utilized in connection with, and the laboratory procedures and techniques of antibody production, hybridoma production, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

Antibody: As used herein, the term "antibody" refers to immunoglobulin molecules and immunologically active portions of immunoglobulin (Ig) molecules, i.e., molecules that contain an antigen binding site that immunologically binds an antigen. Antibodies include, but are not limited to, polyclonal, monoclonal, chimeric, dAb (domain antibody), single chain, $F_{ab}$, $F_{ab'}$, and $F_{(ab')2}$ fragments, single-chain Fv fragments (scFvs), and an $F_a$, expression library. The basic antibody structural unit is known to comprise a tetramer. Each tetramer is composed of two identical pairs, of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

Monoclonal Antibody: The term "monoclonal antibody" (MAb) or "monoclonal antibody composition", as used herein, refers to a population of antibodies that contain only one species consisting of a unique light chain gene product and a unique heavy chain gene product. In particular the complementary determining regions (CDRs) of the monoclonal antibody are identical in all the molecules of the population. MAbs contain an antigen binding site capable of immunologically binding a particular epitope of the antigen characterized by a unique binding affinity for it.

Antigen Binding Site/Binding Portion: The term "antigen-binding site" or "binding portion" refers to the part of the antibody molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found, between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementary-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al., Nature 342:878-883 (1989). Guidelines for the identification of CDRs is available at http://www.bioinf.org.uk/abs/#cdrid.

Epitope: As used herein, the term "epitope" includes any protein determinant of an antigen capable of specifically binding an antibody or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; preferably ≤100 nM and most preferably ≤10 nM. Biologically active derivatives of the $\gamma^{377-395}$ epitope CKKTTMKI-IPFNRLTIG (SEQ ID NO:18) can be determined as provided by those of skill in the art. See, e.g., Ugarova et al., Identification of a novel recognition sequence for integrin $\alpha_M\beta_2$ within the γ-chain of fibrinogen. J Biol Chem. 1998; 273: 22519-22527; Ugarova et al. Recognition of fibrinogen by leukocyte integrins. Ann N Y Acad Sci. 2001; 936:368-385.

Immunological Binding: As used herein, the terms "immunological binding," and "immunological binding properties" refer to the non-covalent interactions of the type which occur between an immunoglobulin molecule and an antigen for which the immunoglobulin is specific. The strength, or affinity, of immunological binding interactions can be expressed in terms of a dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361: 186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to the fibrinogen $\gamma^{377-393}$ epitope when the equilibrium binding constant ($K_d$) is ≤1 µM, preferably ≤100 nM, more preferably ≤10 nM, and most preferably ≤100 pM to about 1 pM, as measured by assays such as radioligand binding assays or similar assay's known to those skilled in the art.

Fibrin and Fibrinogen: As use herein, the terms "fibrin" and "fibrinogen" are used interchangeably and refers to a polypeptide, fragment, or analog that retains Mac-1 binding ability. Fibrinogen is a soluble precursor to fibrin and both retain the γC domain, and thus the epitopes of the present invention.

Isolated Polynucleotide: The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

Isolated Protein: The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, (3) is expressed by a cell from a different species, or (4) does not occur in nature.

Polypeptide: The term "polypeptide" is used herein to refer to a native proteins, protein fragments, and fragments or analogs of a polypeptide sequence. Native protein fragments and analogs are considered species of the polypeptide genus. Examples of polypeptides in accordance with the present invention include the light chain immunoglobulin molecule represented as SEQ ID NO: 1 and the heavy chain immunoglobulin molecule represented as SEQ ID NO: 5, as well as the CDRs represented as SEQ ID NOs: 2, 3, 4, 6, 7 and 8, antibody molecules formed by combinations comprising the heavy chain immunoglobulin molecules with light chain immunoglobulin molecules, such as kappa light chain immunoglobulin molecules, and vice versa, as well as fragments and analogs thereof.

Naturally-Occurring: The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

Operably Linked: The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

Control Sequence: The term "control sequence" as used herein refers to polynucleotide sequences which are necessary to effect the expression and processing of coding sequences to which they are ligated. The nature of such control sequences differs depending upon the host organism. In prokaryotes, such control sequences generally include promoter, ribosomal binding site, and transcription termination sequence. In eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

Polynucleotide: As used herein, the term "polynucleotide" means a polymeric compound of nucleotides of at least 10 bases in length, either ribonucleotides or deoxyribonucleotides or a modified form of either type of nucleotide. The term includes single; and double stranded forms of DNA.

Oligonucleotide: As used herein, the term oligonucleotide includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides, of the invention are either sense or antisense oligonucleotides.

Naturally Occurring Nucleotides: As used herein, the term "naturally occurring nucleotides" includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphoroselerloate, phosphoroanilothioate, phoshoraniladate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

Selectively Hybridize: As used herein, the term "selectively hybridize" means to detectably and specifically bind. Polynucleotides, oligonucleotides and fragments thereof in accordance with the invention selectively hybridize to nucleic acid strands under hybridization and wash conditions that minimize appreciable amounts of detectable binding to non-specific nucleic, acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologous of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionary related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence, relationships between two or more polynucleotide or amino acid sequences: "reference sequence", "comparison window", "sequence identity", "% age of sequence identity", and "substantial identity".

Reference Sequence: A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity.

Comparison Window: A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20% or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest % age of homology over the comparison window) generated by the various methods is selected.

Sequence Identity: The term "sequence identity" means that two polynucleotide or amino acid sequences are identical (i.e., on a nucleotide-by-nucleotide or residue-by-residue basis) over the comparison window. The term "% age of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the % age of sequence identity. The terms "substantial identity" as used herein denotes a characteristic of a polynucleotide or amino acid sequence, wherein the polynucleotide or amino acid comprises a sequence that has at least 85% sequence identity, preferably at least 90 to 95% sequence identity, more usually at least 99% sequence identity as compared to a reference sequence over a comparison window of at least 18 nucleotide (6 amino acid) positions, frequently over a window of at least 24-48 nucleotide (8-16 amino acid) positions, wherein the % age of sequence identity is calculated by comparing the reference sequence to the sequence which may include deletions or additions which total 20% or less of the reference sequence over the comparison window. The reference sequence may be a subset of a larger sequence.

Amino Acids: As used herein, the twenty conventional amino acids and their abbreviations follow conventional usage. See Immunology-A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, α-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention. Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

Substantial Identity: As applied to polypeptides, the term "substantial identity" means that two peptide sequences, when optimally aligned, such as by the programs GAP or BESTFIT using default gap weights, share at least 80% sequence identity, preferably at least 90% sequence identity, more preferably at least 95% sequence identity, and most preferably at least 99% sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. Certain percentages in between are included, such as 75%, 76%, 77%, 78%, 79% 80%, 81%, 82%, 83%, 84%, 85%, 86%, 87%, 88%, 89%, 90%, 91%, 92%, 93%, 94%, 95%, 96%, 97%, 98%, and 99% sequence identity. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur, near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1990); and Thornton et al. Nature 354:105 (1991).

Polypeptide Fragment: As used herein, the term "polypeptide fragment" refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long more preferably at least 20 amino acids long, usually at least 50 amino acids long, and even more preferably at least 70 amino acids long. The term "analog" as used herein refers to polypeptides, which are comprised of a segment of at least 5 amino acids that has substantial identity to a portion of a deduced amino acid sequence and which has specific binding to a fibrin $\gamma^{377-395}$ epitope, CKKTTMKIIPFNRLTIG (SEQ ID NO:18), or a biologically active derivative thereof under suitable binding conditions. Typically, polypeptide analogs comprise a conservative amino acid substitution (or addition or deletion) with respect to the naturally-occurring sequence. Analogs typically are at least 5 amino acids long, preferably at least 10 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

Agent: As used herein, the term "agent" denotes a chemical compound a mixture of chemical compounds, a biological macromolecule, or an extract made from biological materials.

Label: As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$, fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

Pharmaceutical Agent or Drug: As used herein, the terms "pharmaceutical agent" or "drug" refer to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

Substantially Pure: As used herein, the term "substantially pure" means an object species is the predominant species present (i.e., on a molar basis it is more abundant than any other individual species in the composition), and preferably a substantially purified fraction is a composition wherein the object species comprises at least about 50%, (on a molar basis) of all macromolecular species present. Generally, a substantially pure composition will comprise more than about 80% of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

Patient: As used herein, the term patient includes human and veterinary subjects.

Monoclonal Antibodies

The present invention provides monoclonal antibodies that inhibit fibrinogen-Mac-1 binding. In particular, the invention provides monoclonal antibodies that specifically bind the $\gamma^{377-395}$ epitope of the fibrin and fibrinogen γC domain. The invention also provides antibodies that bind the $\gamma^{190-202}$ epitope of the fibrin and fibrinogen γC domain. Such antibodies block the damaging effects of fibrin in the nervous system without affecting its beneficial effects in blood coagulation. These monoclonal antibodies can block formation, of MS plaques and certain cancers. Exemplary antibodies of the invention include, for example, the 5B8 antibody (targeting the $\gamma^{377-395}$ epitope). In addition, antibodies of the invention include, for example, the 1E3 antibody (targeting the $\gamma^{190-202}$ epitope). Various polynucleotide and polypeptide sequences related to the 5B8 antibody, and uses of such sequences are provided herein. These sequences include the 5B8 light chain amino acid sequence (SEQ ID NO:1), three light chain CDR amino acid sequences (CDR-L1, SEQ ID NO:2; CDR-L2, SEQ ID NO:3; and CDR-L3, SEQ ID NO:4), heavy chain amino acid sequence (SEQ ID NO:5), three heavy chain CDR amino acid sequences (CDR-H1, SEQ NO:6; CDR-H2, SEQ ID NO:7; and CDR-H3, SEQ ID NO:8), light chain nucleotide sequence (SEQ ID NO:9), heavy chain nucleotide sequence (SEQ ID NO:10), nucleotide sequences of the three light chain CDRs (CDR-L1, SEQ ID NO:11; CDR-L2; SEQ ID NO:12; and CDR-L3, SEQ ID NO:13), and nucleotide sequences of the three heavy chain CDRs (CDR-H1, SEQ ID NO:14; CDR-H2, SEQ ID NO: 15; and CDR-H3, SEQ ID NO:16).

Monoclonal antibodies of the invention have the ability to inhibit phagocytosis in vitro and in vivo, block cytokine release and macrophage activation in vitro and in vivo, microglia activation in vitro and in vivo, inflammatory demyelination in vitro and in vivo, and clinical symptoms in Experimental Autoimmune Encephalomyelitis (EAE), an animal model of Multiple Sclerosis. See, e.g., PCT Publication WO 2007/0384007 incorporated herein by reference in its entirety. Those of skill in the art will also recognize that the monoclonal antibodies of the present invention can also affect cancer. See, e.g., PCT Publication WO 2007/024817 incorporated by reference herein in its entirety. In addition, such monoclonal antibodies could be used in the treatment of diseases that involve fibrinogen leakage from damaged tissues including Rheumatoid Arthritis, spinal cord injury, Alzheimer's Disease, and stroke. See, e.g., Flick et al., J. Clin. Investigation, 2007, 117, 11:3224-3235; Akassoglou et al., 2002, Neuron, 33:861-875; Akassoglou et al., 2004, Proc. Natl. Acad. Sci. USA, 101:6698-6703; Adams et al., 2007, J. Exp. Med., 35:2428-34. It should be noted that the monoclonal antibodies of the present invention reduce the pro-inflammatory affects of fibrinogen in the brain and elsewhere in a subject while at the same time retaining the beneficial effects of fibrinogen in blood clotting, unlike compounds that affect blood clotting.

Also included in the invention are antibodies that bind to the same epitopes as the antibodies described herein. Those skilled in the art will recognize that it is possible to determine, without undue experimentation, if a monoclonal antibody has the same specificity as a monoclonal antibody of the invention by ascertaining whether the former prevents the latter from binding to the $\gamma^{377-395}$ epitope or the $\gamma^{190-202}$ epitope of the of the fibrin γC domain. If the monoclonal antibody being tested competes with the monoclonal antibody of the invention, as shown by a decrease in binding by the monoclonal antibody of the invention, then it is likely that the two monoclonal antibodies bind to the same, or a closely related, epitope. Screening of monoclonal antibodies of the invention can be carried out by measuring the ability to block microglial adhesion via the Mac-1 receptor on full length fibrinogen polypeptide. Examples of such screening are provided herein.

Various procedures known within the art may be used for the production of polyclonal or monoclonal antibodies directed against fibrinogen-Mac-1 binding, or against derivatives, fragments, analogs homologs or orthologs thereof. (See, for example, Antibodies: A Laboratory Manual, supra).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography.

The antibodies of the invention (e.g., 5B8 and 1E3) are monoclonal antibodies. Monoclonal antibodies that inhibit fibrinogen/Mac-1 binding are generated, e.g., by clones obtained from animals that have been immunized with a peptide antigen. The cell lines are produced by fusing B cells from the immunized animal with myeloma cells. Antibodies are purified either in vitro from the media of from production of ascites in mice. Methods of producing antibodies are also provided in the Examples section below.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an, immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can to cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as FIAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, Anal. Biochem., 107:220 (1980); Patrono, C. and Peskar, B. A. (eds) Radioimmunoassay in Basic and Clinical Pharmacology. Heidelberg, Springer-Verlag, 1987; Dwenger, A. Radioimmunoassay: An Overview. J Clin Biochem 22:883, 1984. *Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, Monoclonal Antibodies: Principles and Practice, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816, 567. DNA encoding the monoclonal antibodies of the invention can be readily isolated and sequenced using conventional procedures (e.g.; by using oligonucleotide probes that are capable of binding specifically to genes encoding the heavy and light chains of murine antibodies). For example, SEQ ID NOs:9 and 10 provide the nucleotide sequences for the 5B8 monoclonal antibody of the present invention. The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from, human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: Monoclonal Antibodies and Cancer Therapy, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: Monoclonal Antibodies and Cancer Therapy, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. In such animals, the endogenous genes encoding the heavy and light immunoglobulin chains in the nonhuman host have been incapacitated, and active loci encoding human heavy and light chain immunoglobulins are inserted into the host's genome. For example, SEQ ID NOs:11 through 16 provide the nucleotide sequences encoding the three light chain and three heavy chain CDRs of monoclonal antibody 5B8. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse® as provided by Amgen (Thousand Oaks, Calif.). This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain (e.g., SEQ ID NO: 10) into one mammalian host cell in culture, introducing an expression vector containing a nucleotide sequence encoding a light chain (e.g., SEQ ID NO: 9) into another mammalian host cell, and fusing the two cells to form a hybrid cell. The hybrid cell expresses an antibody containing the heavy chain and the light chain.

The antibody can be expressed by a vector containing a DNA segment encoding the single chain antibody described above.

These can include vectors, liposomes, naked DNA, adjuvant-assisted DNA gene gun, and catheters. Preferred vectors include viral vectors, fusion proteins and chemical conjugates. Retroviral vectors include moloney murine leukemia viruses. DNA viral vectors are preferred. These vectors include pox vectors such as *orthopox* or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci. U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cell cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell, microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icv) infusion using a minipump infusion system, such as a SynchroMed Infusion System (Medtronic, Minneapolis, Minn.). Other methods that can be used include catheters, intravenous, parenteral, intraperitoneal and subcutaneous injection, and oral or other known routes of administration.

These vectors can be used to express large quantities of antibodies that can be used in a variety of ways. For example, the antibodies can be used to detect the presence of fibrinogen and fibrinogen/Mac-1 binding.

Techniques can be adapted for the production of single-chain antibodies specific to an antigenic protein of the invention (see, e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments. The invention also includes $F_v$, $F_{ab}$, $F_{ab'}$ and $F_{(ab')2}$ anti-fibrin $\gamma^{190-202}$ and $\gamma^{377-395}$ fragments, single chain anti-$\gamma^{190-202}$ and $\gamma^{377-395}$ fibrin antibodies, bispecific anti-$\gamma^{190-202}$ and $\gamma^{377-395}$ fibrin antibodies and heteroconjugate anti-$\gamma^{190-202}$ and $\gamma^{377-395}$ fibrin antibodies.

Bispecific antibodies are antibodies that have binding specificities for at least two different antigens. In the present case, one of the binding specificities is for the $\gamma^{190-202}$ and $\gamma^{377-395}$ fibrin epitope. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

Bispecific antibodies can be prepared as full length antibodies or antibody fragments (e.g., $F_{(ab')2}$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate $F_{(ab')2}$ fragments. These fragments are reduced in the presence of the dithiol complexing agent sodium arsenide to stabilize vicinal dithiols and prevent intermolecular disulfide formation. The $F_{ab'}$ fragments generated are then converted to thionitrobenzoate (TNB) derivatives. One of the $F_{ab'}$-TNB derivatives is then reconverted to the Fab'-thiol by reduction with mercaptoethylamine and is mixed with an equimolar amount of the other $F_{ab'}$-TNB derivative to form the bispecific antibody. The bispecific antibodies produced can be used as agents for the selective immobilization of enzymes.

Additionally, $F_{ab'}$ fragments can be directly recovered from *E. coli* and chemically coupled to form bispecific antibodies. Shalaby et al., J. Exp. Med. 175:217-225 (1992) describe the production of a fully humanized bispecific antibody $F_{(ab')2}$ molecule.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valences are contemplated. For example, trispecific antibodies can be prepared. Tutt et al., J. Immunol. 147:60 (1991).

The invention also pertains to immunoconjugates comprising an antibody conjugated to a cytotoxic agent such as a toxin (e.g., a chemotherapeutic agent targeting cancerous cells, an enzymatically active toxin of bacterial, fungal, plant, or animal origin, or fragments thereof), or a radioactive isotope (i.e., a radioconjugate). Examples of chemotherapeutic agents include Alkylating Agents, Nitrosoureas, Antimetabolites, Anthracyclines and Related Drugs, Topoisomerase Inhibitors, Mitotic Inhibitors, Corticosteroid Hormones and other chemotherapy drugs.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officials inhibitor, gelonin, mitogellin, restriction, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate); aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin, immunotoxin can be prepared as described in Vitetta et al., Science 238: 1098 (1987). Carbon-14-labeled 1-isothiocyanatobenzyl-3-methyldiethylene, triaminepentaacetic acid (MX-DTPA) is an exemplary chelating agent for conjugation of radionucleotide to the antibody.

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), incorporated herein by reference in its entirety).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987).

Linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Exemplary linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyldithio)-toluene (Pierce Chem. Co., Cat. (21558G); (iii) SPDP (succinimidyl-6[3-(2-pyridyldithio) propionamido]hexanoate (Pierce Chem. Co., Cat #21651G); (iv) Sulfo-LC-SPDP (sulfosuccinimidyl 6[3-(2-pyridyldithio)-propianamide]hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. $F_{ab'}$ fragments of the antibody of the present invention can be conjugated to the liposomes as described in Martin et al., J. Biol. Chem., 257: 286-288 (1982) via a disulfide-interchange reaction.

Use of Antibodies Against the Fibrin Epitopes $\gamma^{190-202}$ and $\gamma^{377-395}$ Therapeutic formulations of the invention, which include a monoclonal antibody of the invention, are used to treat or alleviate a symptom associated with a fibrin-related disorder (e.g., multiple sclerosis, wound healing, lung ischemia, spinal cord injury, Alzheimer's Disease, stroke, Rheumatoid Arthritis and cancer), preferably without affecting blood coagulation. The present invention also provides methods of treating or alleviating a symptom associated with a fibrin-related disorder (e.g., multiple sclerosis, wound healing, lung ischemia, spinal cord injury, Alzheimer's Disease, stroke, Rheumatoid Arthritis and cancer), preferably without affecting blood coagulation. A therapeutic regimen is carried out by identifying a subject, e.g., a human patient suffering from (or at risk of developing) a fibrin-related disorder (e.g., multiple sclerosis, wound healing, lung ischemia, spinal cord injury, Alzheimer's Disease, stroke, Rheumatoid Arthritis and cancer), using standard methods. Symptoms associated with these fibrin-related disorders include, for example, inflammation, pain and loss of sensory perception. Efficaciousness of treatment is determined in association with any known method for diagnosing or treating the particular fibrin-related disorder. Alleviation of one or more symptoms of the fibrin-related disorder indicates that the antibody confers a clinical benefit. An antibody preparation, preferably one having high specificity and high affinity for its target antigen, is administered to the subject and will generally have an effect due to its binding with the target. Administration of the antibody may abrogate or inhibit or interfere with the signaling function of the target (e.g., the $\gamma^{190-202}$ and $\gamma^{377-395}$ fibrin epitopes). Administration of the antibody may abrogate or inhibit or interfere with the binding of the target (e.g., fibrin) with an endogenous ligand (e.g., Mac-1) to which it naturally binds. For example, the antibody binds to the target and inhibits fibrin/Mac-1 binding.

t will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary Remington's Pharmaceutical Sciences (19th ed, Mack Publishing Company, Easton, Pa. (1995)), particularly Chapter 87 by Blaug, Seymour, therein. These formulations include, for example, powders, pastes, ointments, jellies, waxes, oils, lipids, lipid (cationic or anionic) containing vesicles (such as Lipofectin™) DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention; provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The antibodies of the invention (also referred to herein as "active compounds"), and derivatives, fragments, analogs and homologs thereof, can be incorporated into pharmaceutical compositions which can comprise a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition can be sterile and should be fluid to the extent that easy syringeability exists. It can be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration can be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid, copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

A therapeutically effective amount of an antibody of, the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibody Screening Methods

Methods for the screening of antibodies that possess the desired specificity include, but are not limited to, enzyme linked immunosorbent assay (ELISA) and other immunologically mediated techniques known within the art.

Antibodies directed against the $\gamma^{190-202}$ and $\gamma^{377-395}$ fibrin epitopes may be used in methods known within the art relating to the localization and/or quantitation of the fibrin. In a given embodiment, antibodies specific to the $\gamma^{190-202}$ and $\gamma^{377-395}$ fibrin epitopes, or derivative, fragment, analog or homolog thereof, that contain the antibody derived antigen binding domain, are utilized as pharmacologically active compounds (referred to hereinafter as "Therapeutics").

An antibody specific for the $\gamma^{190-202}$ and $\gamma^{377-395}$ fibrin epitopes can be used to isolate the fibrin polypeptide by standard techniques, such as immunoaffinity, chromatography or immunoprecipitation. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An antibody according to the invention can be used as an agent for detecting the presence of the $\gamma^{190-202}$ and/or $\gamma^{377-395}$ fibrin epitopes in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Inhibitor Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the binding of fibrin and Mac-1, or candidate or test compounds or agents that modulate or otherwise interfere with the signaling function of fibrin, Mac-1 and/or the fibrin/Mac-1 complex. The invention also includes compounds identified in the screening assays described herein.

In one embodiment, the invention provides assays for screening candidate or test compounds which modulate the signaling function of the fibrin/Mac-1 complex and/or the interaction between fibrin and Mac-1. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37:1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233, 409.).

In one embodiment, a candidate compound is introduced to an antibody-antigen complex and determining whether the candidate compound disrupts the antibody-antigen complex, wherein a disruption of this complex indicates that the candidate compound modulates the signaling function of the fibrin/Mac-1 complex and/or the interaction between fibrin and Mac-1. For example, the monoclonal antibody 5B8 and the antigen fibrinogen complex. Alternatively, the monoclonal antibody is 1E3 and the antigen is the fibrinogen.

In another embodiment, a fibrin/Mac-1 complex is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with fibrin/Mac-1 binding.

In another embodiment, a soluble chimeric protein of the invention is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with fibrin/Mac-1 binding.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability, of the antigen to bind to or interact with the antibody in the presence of the test compound.

Those skilled in the art will recognize that, in any of the screening methods disclosed herein, the antibody may be a neutralizing antibody, such as monoclonal antibody 5B8 and/or 1E3, each of which modulates or otherwise interferes with fibrin/Mac-1 binding.

In one embodiment, it may be desirable to immobilize either the antibody, or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody (e.g. 5B8 and/or 1E3) or the antigen (e.g. fibrin) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a sandwich assay can be performed in which full-length fibrinogen, fibrin or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest (e.g. monoclonal antibody 5B8 and/or 1E3) bound to the immobilized polypeptide is subsequently incubated with a second, labeled antibody or antibody bound to a coupling agent such as biotin or avidin. This second antibody may be another, anti-fibrin antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

An exemplary method for detecting the presence or absence of a fibrin protein in a biological sample involves obtaining a biological sample from a test subject and contacting the biological sample with a labeled monoclonal antibody according to the invention such that the presence of fibrin is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect fibrin in a biological sample in vitro as well as in vivo. For example, in vitro techniques for detection of fibrin include enzyme linked immunosorbent assays (ELISAs), Western blots, immuno-precipitations, and immunofluorescence. Furthermore, in vivo techniques for detection of fibrin include introducing into a subject a labeled anti-fibrin antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

Kits

The invention also encompasses kits for detecting the presence of fibrin in a biological sample. For example, the kit can comprise: a labeled compound or agent capable of detecting fibrin in a biological sample; means for determining the amount of fibrin in the sample; and means for comparing the amount of fibrin in the sample with a standard. The compound or agent can be packaged in a suitable container. The kit can further comprise instructions for using the kit to detect fibrin in a sample.

The invention will be further described in the following examples, which do not limit the scope of the invention described in the claims.

EXAMPLES

Aspects of the present teachings may be further understood in light of the following examples, which should not be construed as limiting the scope of the present, teachings in any way.

Example 1

Generation of Monoclonal Antibodies

Peptide sequences corresponding to the exact amino acids on the γ chain of fibrinogen that have been shown to be critical for the interaction of fibrinogen with Mac-1 were synthesized (Peptide #1: CGWTVLQKRIDGSL (SEQ TD NO:17) and Peptide #2: CKKTTMKIIPFNRLTIG (SEQ ID NO:18)). These two peptides were synthesized with corresponding N-terminal cysteine residues to allow for conjugation to the carrier protein keyhole limpet hemocyanin (KLH) which promotes a robust antibody response in vivo. Both peptides were used to immunize three mice generating an antibody response in these mice. Preliminary serum screening revealed a strong antibody titer against these peptides and lead to the subsequent generation of hybridomas producing clonal antibodies against these two peptide sequences. The initial screening of 480 hybridoma clones was performed by ELISA against both peptides as well as the carrier protein. The positive clones were expanded and retested to confirm peptide epitope reactivity by ELISA. The final results of this initial screen resulted in 46 clones that were specific to either Peptide #1 or #2. In depth analysis of these ELISA results identified 16 target candidates for further examination. These 16 clones were screened for their ability to block microglial adhesion via the Mac-1 receptor on full length fibrinogen. Tissue culture wells were coated with 50 µg/mL fibrinogen upon which microglia cells (200,000 cells/mL) were plated in the presence of these antibody clones. Wells were, washed after 30 minutes and the remaining adherent cells were stained with 0.1% crystal violet. Stained cells were fixed with 1% PFA and solubilized with 0.5% Triton X-100. Five of these clones showed a significant ability, similar to that of a commercially available blocking antibody to Mac-1 (M1/70), to prevent microglial adhesion to fibrinogen as assessed by absorbance measurements at 595 nm (FIG. 1; having greater than 20% inhibition as measured by shift in absorbance). It is contemplated that antibodies of the invention can prevent microglial adhesion to fibrinogen at greater than 30%, 40%, or 50%. Clones 1A5, 1D6 and 1E3 recognize the Peptide #1 epitope while clones 4E11 and 5B8 recognize the Peptide #2 epitope. These five clones were further analyzed for their ability to recognize fibrinogen by western blot. All five antibodies recognized fibrinogen's γ chain to a similar degree. To examine whether these antibodies recognized fibrinogen in a dose dependent manner an ELISA was performed on full length coated fibrinogen (FIG. 2). All five antibodies were found to specifically bind increasing concentrations of full length fibrinogen. From these five antibodies three were chosen (1E3, 4E11 and 5B8, having greater than 50% inhibition of Mac-1 binding to the fibrin or fibrinogen γC domain when measured by shift in absorbance) for isolation and large scale purification. It is contemplated that antibodies of the invention can inhibition of Mac-1 binding to the fibrin at greater than 50%, 60% or 70%. Initially, 20 mg of all three antibodies were purified for use in in vitro phagocytosis assays and in EAE experiments.

Example 2

Monoclonal Antibodies Against the γ Chain of Fibrinogen Inhibit Phagocytosis by Microrglia Phagocytosis is a major function of activated microglia and macrophages that is mediated by Mac-1. Phagocytosis assays were performed on microglia as previously described. See, Adams et al., 2007, J. Exp. Med. 204:571-582, incorporated herein by reference in its entirety. The fibrin-derived $\gamma^{377-395}$ peptide inhibits microglia activation and suppresses relapsing paralysis in central nervous system autoimmune disease. The monoclonal antibody 5B8 against the modified fibrin $\gamma^{377-395}$ epitope showed superior efficacy in inhibiting phagocytosis in vitro. This antibody in in vivo studies shows a prophylactic and therapeutic administration in animal models for MS as was previously described for the $\gamma^{377-395}$ peptide.

Example 3

Monoclonal Antibody 5B8 Suppresses Relapses Incidence in a Remitting-Relapsing Animal Model of Experimental Autoimmune Encephalomyelitis To assess the effects of the fibrin antibodies in the regulation of microglia activation and demyelination in vivo, two of the clones identified in the phagocytosis assay to mice after the development of PLP EAE were administered. Antibodies 5B8 and 4E11 were administered three times per week at 250 μg per mouse. As shown in FIG. 4, the antibody 4E11 did not have a substantial effect in the development of EAE. By contrast, the antibody 5B8 showed a suppression of clinical symptoms at the time of the relapse.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

Citation of a reference herein shall not be construed as an admission that such is prior art to the present invention.

What is claimed is:

1. An isolated antibody that binds human fibrin or fibrinogen γC domain, and inhibits Mac-1 binding to fibrin or fibrinogen γC domain, wherein the antibody light chain comprises three complementarity determining regions comprising the amino acid sequences of RSSKSLLHSSGITYLS (SEQ ID NO:2), QMSNLAS (SEQ ID NO:3), and AQNLELPLT (SEQ ID NO:4), respectively, and the antibody heavy chain comprises three complementarity determining regions comprising the amino acid sequences of GYTFTSYWIH (SEQ ID NO:6), LIDPSDSYTNYNQKFRG (SEQ ID NO:7), and SDPTGC (SEQ ID NO:8), respectively.

2. The antibody of claim 1, wherein the antibody is a humanized antibody.

3. The antibody of claim 1, wherein the antibody binds an $\gamma^{377-395}$ epitope (SEQ ID NO:18) of the fibrin or fibrinogen γC domain.

4. The antibody of claim 1, wherein the antibody suppresses clinical symptoms of Experimental Autoimmune Encephalomyelitis (EAE).

5. The antibody of claim 1, wherein the antibody exhibits greater than 20% inhibition of microglial adhesion to the fibrin or fibrinogen γC domain.

6. The antibody of claim 1, wherein the antibody exhibits greater than 50% inhibition of Mac-1 binding to the fibrin or fibrinogen γC domain.

7. A pharmaceutical composition comprising the antibody of claim 1 and a pharmaceutically acceptable carrier.

8. An isolated antibody, wherein the antibody binds human fibrin or fibrinogen γC domain, and inhibits Mac-1 binding to fibrin or fibrinogen γC domain, and wherein the antibody light chain variable domain comprises the amino acid sequence of SEQ ID NO:1.

9. The antibody of claim 8, wherein said antibody comprises the heavy chain variable domain comprising the amino acid sequence of SEQ ID NO:5.

10. The antibody of claim 8, wherein the antibody is a chimeric antibody.

11. The antibody of claim 8, wherein the antibody binds an $\gamma^{377-395}$ epitope (SEQ ID NO:18) of the fibrin or fibrinogen γC domain.

12. The antibody of claim 8, wherein the antibody suppresses clinical symptoms of Experimental Autoimmune Encephalomyelitis (EAE).

13. The antibody of claim 8, wherein the antibody exhibits greater than 20% inhibition of microglial adhesion to the fibrin or fibrinogen γC domain.

14. The antibody of claim 8, wherein the antibody exhibits greater than 50% inhibition of Mac-1 binding to the fibrin or fibrinogen γC domain.

15. A pharmaceutical composition comprising the antibody of claim 8 and a pharmaceutically acceptable carrier.

16. An isolated antibody wherein the antibody binds human fibrin or fibrinogen γC domain, and inhibits Mac-1 binding to fibrin or fibrinogen γC domain, and wherein the antibody heavy chain variable domain comprises the amino acid sequence of SEQ ID NO:5.

17. The antibody of claim 16, wherein the antibody is a chimeric antibody.

18. The antibody of claim 16, wherein the antibody binds an $\gamma^{377-395}$ epitope (SEQ ID NO:18) of the fibrin or fibrinogen γC domain.

19. The antibody of claim 16, wherein the antibody suppresses clinical symptoms of Experimental Autoimmune Encephalomyelitis (EAE).

20. The antibody of claim 16, wherein the antibody exhibits greater than 20% inhibition of microglial adhesion to the fibrin or fibrinogen γC domain.

21. The antibody of claim 16, wherein the antibody exhibits greater than 50% inhibition of Mac-1 binding to the fibrin or fibrinogen γC domain.

22. A pharmaceutical composition comprising the antibody of claim 16 and a pharmaceutically acceptable carrier.

* * * * *

UNITED STATES PATENT AND TRADEMARK OFFICE
CERTIFICATE OF CORRECTION

PATENT NO. : 8,877,195 B2  
APPLICATION NO. : 13/425020  
DATED : November 4, 2014  
INVENTOR(S) : Katerina Akassoglou Page 1 of 1

It is certified that error appears in the above-identified patent and that said Letters Patent is hereby corrected as shown below:

In the Specification

STATEMENT REGARDING FEDERALLY SPONSORED RESEARCH OR DEVELOPMENT, Column 1, Lines 14-16, delete:
"This invention was made in part with government support under NS052189 awarded by National Institute of Health. The government has certain rights in the invention."

And insert:
--This invention was made with government support under NS052189 awarded by the National Institutes of Health. The government has certain rights in the invention.--

Signed and Sealed this  
Third Day of February, 2026

John A. Squires  
*Director of the United States Patent and Trademark Office*